United States Patent [19]

Landwehr et al.

[11] Patent Number: 4,928,708
[45] Date of Patent: May 29, 1990

[54] REPRODUCING HUMAN POSTURE

[76] Inventors: Ulrich M. Landwehr, Bahnhofstrasse 8, D-3000 Hannover; Guenter Rackwitz, Berliner Allee 9, D-3162 Uetze/Dolbergen, both of Fed. Rep. of Germany

[21] Appl. No.: 186,621

[22] Filed: Apr. 27, 1988

[30] Foreign Application Priority Data

Apr. 27, 1987 [DE] Fed. Rep. of Germany ....... 3714015

[51] Int. Cl.$^5$ ................................................ A61B 5/10
[52] U.S. Cl. .................................... 128/774; 128/779; 128/782
[58] Field of Search ......................... 128/774, 779, 782

[56] References Cited

U.S. PATENT DOCUMENTS 2,052,789  9/1936  Moss et al. ........................... 128/782
3,826,145  7/1974  McFarland ........................... 128/782

FOREIGN PATENT DOCUMENTS 454898  6/1975  U.S.S.R. ............................... 128/782

Primary Examiner—Kyle L. Howell
Assistant Examiner—John C. Hanley
Attorney, Agent, or Firm—Ralf H. Siegemund

[57] ABSTRACT

A stand for reproducibly ascertaining the posture of a free-standing human being, includes a base plate, a central bending post and a standing plate affixed to the central post; the standing plate exerts tension upon the central post particularly when a person stands on the plate; strain gauges are affixed to the central post and the stand as a whole is improved by providing a pair of foot plates placed side by side, each foot plate is supported by a pair of rotatable tubular elements or rings on the stand plate, for elevationally adjustably mounting the respective foot plate; all these elements are driven in unison by a belt such that one foot plate is raised while the other one is lowered and vice versa.

16 Claims, 2 Drawing Sheets

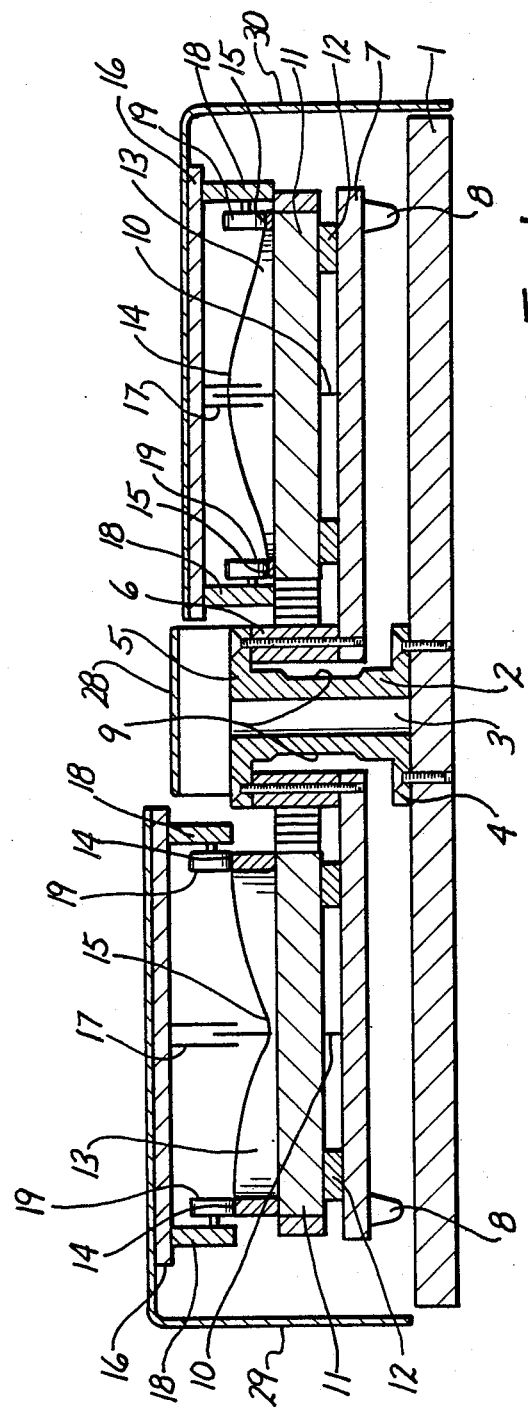
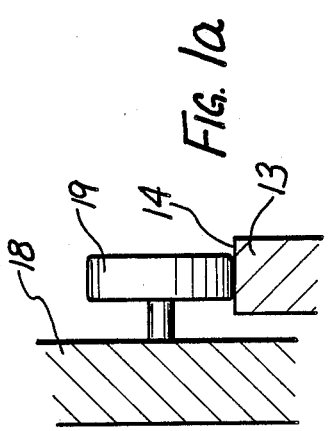
FIG. 1
FIG. 1a

REPRODUCING HUMAN POSTURE

BACKGROUND OF THE INVENTION

The present invention relates to a device and equipment for attaining reproducable measurements and representations of the posture of a free-standing human being, wherein particularly gravity forces, exerted by the human, are transmitted, possibly asymmetrically, upon a measuring structure which includes a base plate and a stand connected to the base plate by means of one or several tension rods, carrying at least two strain gauges.

Generally speaking, devices are known in the field of orthopedics to exactly ascertain damage to the motion apparatus of a person. In order to accomplish this diagnostic data, they are acquired either by themselves or in conjunction with therapy or, for example, repeatedly, e.g. following surgery in order to ascertain progress or lack of it in the recovery and improvement in the mobility of that person. Here, one employs photography as well as X-rays. It is apparent that, in order to provide measurements which are to be compared with others (earlier ones, later ones, etc.), for purposes of evaluating such progress or lack of it, it is clear that the person must assume the some posture. For example, if the person is photographed in different phases of the therapy, then the posture much be the same or the person must be made to attempt to assume the same posture, in order to provide comparable results. However, "same" in this context must be objectivized.

Here then, it was known to provide a structure in which a standing plate is supported by at least two measuring points. These "points" are constructed either as compression sensors or strain gauges, or the like. This known structure, however, is disadvantaged by the fact that a balanced position of a person is attainable only in a frontal plane, from left to right, but not, at the same time, in the sagittal plane. Hence, this known structure does not permit a reproducable centering of the posture of the human being with reference to a point. Moreover, for measuring imbalance, just in one plane, one needs at least two measuring points. In addition, the known structure is disadvantaged by the fact that owing to the direct mounting of the standing plate on the measuring elements, there is a fairly high susceptibility to equipment damage. Also, it was found that rather expensive temperature compensated amplifiers, operating with carrier frequency modulation, have to be used.

An improved device has become known through the German printed patent application P 33 01 864 (see also Canadian Pat. No. 1,227,632). Here, a particular advantageous example includes two parallel plates, namely a base plate and a stand plate, spaced apart from each other and held in position through a bending rod. Strain gauges are affixed to that rod and upon tilting of the stand plate, the rod bends and the gauges, and electrical amplifiers respond. Bending, of course, is the result of an unbalanced posture, not just in the frontal, but also in the sagittal plane. Indeed, this is a definite improvement over the earlier art.

It is also known that incorrect postures result, for example, from different length of the legs of the person, or because of a oblique position of the pelvis. These defects can be corrected through, for example, orthopedic shoes with differently thick soles, or different thick inserts. However, it can readily seen that ascertaining the degree of sole thickness or of the thickness of the insert is rather cumbersome if the above-mentioned device is used, even in the improved version. Moreover, this method is not only cumbersome but also not too accurate. The procedure involves basically the insertion of supplemental standardized plates under the foot on that side which is to be lifted for any reason. The number of these plates added to that side simply is determined by the condition to be compensated. Of course, this requires that the patient, again, has to be checked afterwards; possibly again and again.

U.S. Pat. Nos. 4,370,039 and 4,639,107 disclose a method and equipment which is traded under the mark "Optimetric", and being provided for replacing X-raying. This method is characterized by the fact that a bundle of horizontally running lines are projected obliquely from above upon the patient. In a rather simple manner, un-evennesses in the surface show readily as deflections of the line projections as reflected by the body of the patient. For purposes of comparison, the doctor will make a picture before, as well as after a therapeutic session, and then compares the two pictures. These references are mentioned here only for completion. The present invention is applicable to that equipment, for objectively ascertaining a correct posture prior to the particular measurements by that apparatus.

DESCRIPTION OF THE INVENTION

It is an object of the present invention to provide a new and improved device for providing reproducible representation of the posture of a human being, under utilization of a base plate, a standing plate, and interposed tension or strain gauges. Such a device is to be particularized, so that therapeutic steps can be taken without requiring the patient to change his or her position. The patient must not be required to leave the structure, nor is the patient even required to lift a foot. The structure, moreover, should be quite rugged, particularly to take up the one-sided impacts, up until about 100 kilograms. Basically, the vertical dimension of the new device should remain the same.

In accordance with the preferred embodiment of the present invention, it is suggested to provide two foot plates on the stand plates, with independent height adjustments.

The inventive structure meets the requirements of the objects, as stated, and there is, moreover, the additional advantage that any necessary therapeutic leg length compensation can be observed directly and recorded as elevational difference in the two foot plates. One may use, for example, a video device which looks at the two foot plates and their relative elevation. However, this method differs from that recording as it is necessary to provide a continuous projection of contour defining lines. Of course, in addition, one can make still pictures and store them appropriately. The foot plates are preferably adjusted as to elevations through wedges.

DESCRIPTION OF THE DRAWINGS

While the specification concludes with claims particularly pointing out and distinctly claiming the subject matter which is regarded as the invention, it is believed that the invention, the objects and features of the invention and further objects, features, and advantages thereof will be better understood from the following description taken in connection with the accompanying drawings in which:

FIG. 1 is a cross-section through a device constructed in accordance with the preferred embodiment of the present invention;

FIG. 1a is an enlarged detail of FIG. 1;

Figure 2:
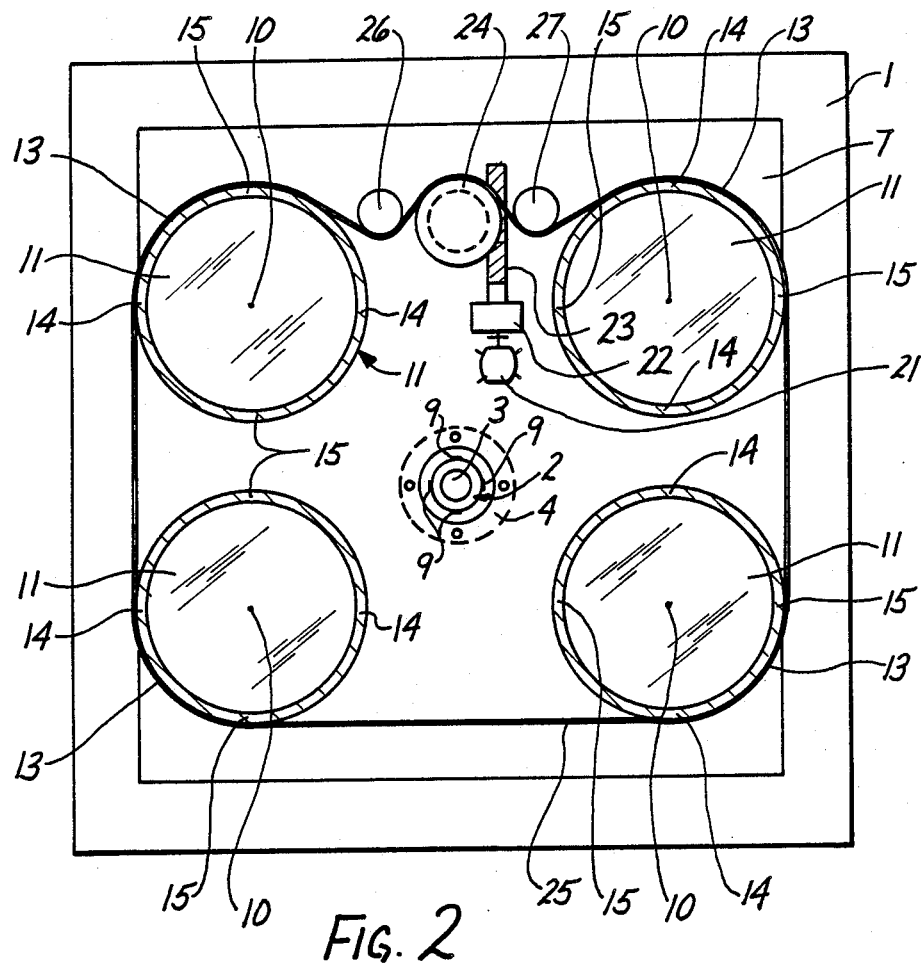
FIG. 2 is an elevational view, partially in section of the same device shown in FIG. 1.

If the stand plate 7 is loaded in an imbalance fashion, rod or tube 2 will bent slightly. In order to avoid excessive bending of rod or tube 2, limiters 8 are provided acting as stops and being interposed between the stand plate 7 and the base plate 1. In order to ascertain the extent, i.e. degree as well as the direction of bending of the rod 2, this rod has four chambered surfaces, being arranged by 90° in relation to each other, and having been milled or filed between the flanges 4 and 5. Strain gauges 9 are fastened to these surfaces. The strain gauges 9 are interconnected by and to an electronic circuit which is not illustrated, and is of conventional design.

Owing to the fact that the rod 2 is provided with a bore 3, i.e. that it is, in effect, constructed as a sleeve, it has a higher mechanical resistance moment, so that in the case of a one-sided imbalance, excessive loading of the strain gauges, and of the electronic circuit is avoided. Rod or tube 2 is dimensioned, so that in the case of an imbalanced load on plate 7, the imbalance being, for example, 100 kilogram, then plate 7 tilts only by about one millimeter, out of the horizontal.

The plate 7 carries and has fastened thereto, four shafts 10, each carrying a gear 11 of the sprocket variety for cooperation with a toothed belt. There are, accordingly, four of these gears 11, and they will engage a toothed transmission belt 25. Rings 12 provide for support of the gear 11. These rings 12 are made of a self-lubricating, pressure (compression) proof material, and are, in fact, interposed between the respective gear 11 and the standing plate 7.

Figure 3:
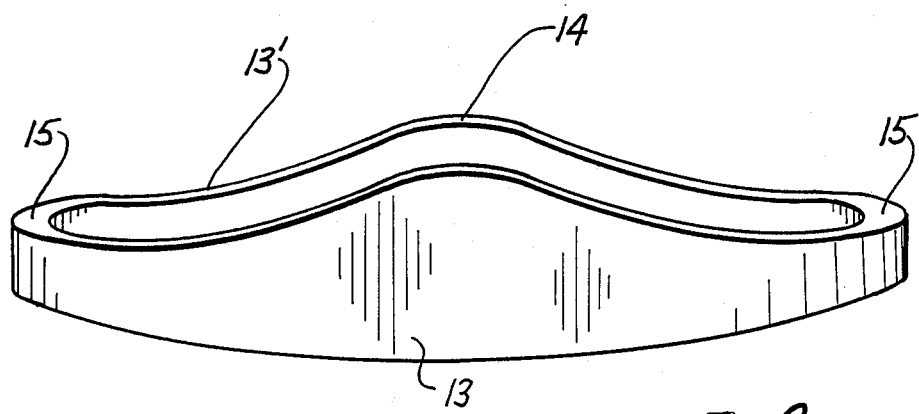
FIG. 3 is a perspective view of one of the four adjusting elements used in the equipment shown in FIGS. 1 and 2. Proceeding now to the detailed description of the drawings, the Figures show a base plate 1, carrying centrally a tubular rod or post 2. This tube, rod, or sleeve 2, is constructed as a double flange element and can be considered to be a rod with a bore 3, there being an upper flange 5 and a lower flange 4, accordingly. Rod or sleeve 2 is preferable made through cutting or milling, or the like, using originally solid material. The rod 2 is fastened to the plate by means of bolts, which are not shown in detail, and are provided, of course, at the lower flange 4. A spacer ring 6, being of a bi-parted configuration, is provided on the under side of the upper flange 5. The ring 6 is bolted to a stand plate 7.

Each of the rings or gears 11 carries a particular ring element 13 by having, so to speak, at its lower side a circular annular flat surface, while the other upper axial end is of a complex contour, as can be seen best from FIG. 3. Along the periphery each ring has two peaks or apices 15, and two valleys 14, a valley alternates with a peak at 90° phase shift, so that the two peaks 15 face each other diametrically, so do the valleys 14. The surface 13′ is, thus, of a kind of wavy configuration. In between any peak and either of its adjoining valleys, the level, so to speak, lowers in uniform manner. Since there are four gears 11, there are four rings 13, accordingly. FIG. 2 shows the arrangement, and on the left-hand side finds the valleys 14, for example, aligned as to two of these rings, while, at the same time, the two right-hand rings have all their peaks 15 aligned. The alignment axes for the right-hand side and the left-hand side, as stated, extend, in this case, in parallel. One can readily see that if each of these rings is turned by 90°, the relationship is reversed. In any event, the high and low points of the left-hand side and the right-hand side are 90° phase shifted.

On each side there is now provided a foot plate 16R and 16L. These plates are held and guided through adequate sleeve guides 17, on upwardly extending shafts 10. The lower side of each of the foot plates carries holders 18 and there are all together four such holders. These holders carry rollers or ball bearings 19 which, in turn, run on the contoured surfaces 13′ of the rings 13. In addition, it has to be mentioned that the foot plates 16 are tensioned vis-a-vis the standing plate 7 through tension springs, which are not illustrated.

All the gears 11 are driven through an electro motor 21, whose output shaft is geared, by means of a transmission 22, and through a spindle 23 for acting upon a drive gear 24. The gear 24 has teeth along its periphery, corresponding to the gear 11. The endless belt 25 engages all of the gears 11, as well as a drive gear 24. Tensioning pulleys 26 and 27 provide engaging tension to the belt 25.

Now, as motor 21 is turned on, the transmission 22 drives the spindle 23, which, in turn, drives the gear 24, and the belt 25 is moved, accordingly. Owing to engagement, all of the gears 11 are now uniformly moved on motion of the belt 25. This movement causes the ball bearing 19 to roll on the surfaces 13′ and either lowers or raises one or the other of the two foot plates 16. Owing to the fact that the foot plates 16R or 16L are held in position by these guide sleeves 17, receiving the shaft 10, it is impossible that any of the plates will tilt out of the way. Again, there should be self-lubricating layering provided inside the sleeve 17.

By covering a range of 90° as far as turning the rings 13 are concerned, the one foot plate will be lifted from a lower-most position to an upper-most position, while the other plate is lowered accordingly. A 45° deflection of all the rings and gears 11 from each of the extreme positions establishes a uniform level for both foot plates 16R and 16L.

There may be, in addition, a cover which provides a connection at the central part 28 to the base 1. On the other hand, side parts 29 and 30 rest on the foot plates 16R and 16L, and are fastened thereto, and therefore, follow the up and down motion of the adjustment as described.

In addition to the foregoing, base plate 1 may, for example, itself be mounted on a turntable or the like, which is motor driven and turns the entire arrangement by 90°. This mounting arrangement permits changing the orientation of the patient as to frontal and sagittal plane, without requiring the patent to move.

The ratio of the drive motor 21 to the revolution of the gears 11 should be at least 30:1, preferably about 100:1. This high reduction in speed produces a certain impediment but it should be noted that the resulting impediment prevents that the gears 11 can actually turn just on loading of the foot plates 16.

The invention offers the significant advantage that in the case of some interference, for example, in the drive, there will be no destruction because of free-wheeling it is permitted owing to the lack of stops.

The invention is not limited to the embodiments described above, but all changes and modifications thereof, not constituting departures from the spirit ad scope of the invention, are intended to be included.

We claim:

1. Apparatus for reproducibly ascertaining the posture of a free-standing human being, including a base plate connected to a central bending post; and a stand plate connected to the central post, and being provided for exerting tension upon the central post, there being strain gauges connected to the central post, the improvement comprising:
   a pair of foot plates; and
   means connected to the stand plate, for elevationally adjustably mounting each of the foot plates to the stand plate.

2. Device as in claim 1, said means for mounting includes structure having an inclined surface so that upon shifting of said structure elevational adjustment of said foot plate adjustment is obtained.

3. Device as in claim 1, said means for mounting including for each foot plate a pair of rings each ring having varying, axial dimensions and being positioned for engaging the foot plates such, that upon turning of the rings by a particular angle, the foot plate is lowered or raised.

4. Device as in claim 3, including common drive means connected to the rings for driving said rings.

5. Device as in claim 1, the mounting means as connected to the two foot plates operating in phase opposition as to the two foot plates.

6. Device as in claim 1, the post being a tube or sleeve with two gauges.

7. Apparatus for reproducibly ascertaining the posture of a free-standing human being and including a base plate connected to a central bending post; a standing plate affixed to the central post, and being provided for exerting tension upon the central post, there being strain gauges affixed to the central post, the improvement comprising:
   a pair of foot plates; and
   means including a pair of rotational element means on the standing plate for elevationally adjustably mounting each foot plate to the stand plate.

8. Device as in claim 7, said rotational elements of the means for mounting including, for each foot plate, a pair of rings with each ring having varying, axial dimensions and both rings of said pair engaging the respective foot plate, and means connected to all said rings for driving the rings in unison such that upon turning of the rings by a particular angle, the two foot plates are lowered and raised in phase opposition.

9. Device as in claim 7, each element is tubular, with an axial end that is of wavy configuration.

10. Device as in claim 9, there being ball or roller bearings interposed between the foot plates and the elements.

11. Device as in claim 8, there being a common toothed belt means for driving all these rings.

12. Device as in claim 11, and including motor and gear means for driving the belt.

13. Device as in claim 12, the motor and gear means providing a transmission ratio in excess of 30:1.

14. Device as in claim 7, each element being contoured to have two maximum and two minimum points, corresponding to high and low positions of the respective foot plate.

15. Device as in claim 7, the post being hollow.

16. Device as in claim 7, and including multiple up and down guide means for each foot plate.

* * * * *